US012544133B2

(12) United States Patent
Mescher et al.

(10) Patent No.: US 12,544,133 B2
(45) Date of Patent: Feb. 10, 2026

(54) APPARATUS AND METHOD FOR COLD PLASMA SKIN RESURFACING

(71) Applicant: Apyx Medical Corporation, Clearwater, FL (US)

(72) Inventors: Megan W. Mescher, Boulder, CO (US); Shawn D. Roman, Safety Harbor, FL (US); Gregory A. Konesky, Hampton Bays, NY (US); Claes Fredrik Jonsson, St. Petersburg, FL (US)

(73) Assignee: Apyx medical corporation, Clearwater, FL (US)

( * ) Notice: Subject to any disclaimer, the term of this patent is extended or adjusted under 35 U.S.C. 154(b) by 1051 days.

(21) Appl. No.: 16/481,296

(22) PCT Filed: Jan. 26, 2018

(86) PCT No.: PCT/US2018/015418
§ 371 (c)(1),
(2) Date: Jul. 26, 2019

(87) PCT Pub. No.: WO2018/140708
PCT Pub. Date: Aug. 2, 2018

(65) Prior Publication Data
US 2019/0336215 A1 Nov. 7, 2019

Related U.S. Application Data

(60) Provisional application No. 62/451,337, filed on Jan. 27, 2017.

(51) Int. Cl.
*A61B 18/20* (2006.01)
*A61B 18/00* (2006.01)
*A61B 18/04* (2006.01)

(52) U.S. Cl.
CPC .......... *A61B 18/203* (2013.01); *A61B 18/042* (2013.01); *A61B 2018/0047* (2013.01);
(Continued)

(58) Field of Classification Search
CPC ................ A61B 18/203; A61B 18/042; A61B 2018/20355; A61B 2018/0047; A61B 2018/00583
See application file for complete search history.

(56) References Cited

U.S. PATENT DOCUMENTS 4,732,755 A * 3/1988 Grana ................ A61L 26/0014 424/78.05
6,350,276 B1 2/2002 Knowlton
(Continued)

FOREIGN PATENT DOCUMENTS

CN 106310524 B 12/2018
WO 2010004403 1/2010
WO 2016114504 A1 7/2016

OTHER PUBLICATIONS

European Search Report for European Application No. 18744300.7; dated Sep. 25, 2020; six (6) pages.
(Continued)

*Primary Examiner* — William J Levicky
*Assistant Examiner* — Jessandra F Hough
(74) *Attorney, Agent, or Firm* — Michael J Porco; Gerald E Hespos

(57) ABSTRACT

An apparatus and method for cold plasma skin resurfacing is provided. In one aspect, a mask for use in fractionated skin resurfacing is provided. The mask includes a plurality of apertures distributed across a surface of the mask. The mask may be made of a flexible material including an adhesive surface, such that the mask may be applied to a contoured surface of a patient's skin while remaining fixed in place.
(Continued)

The material is resistant to the effects of a cold plasma beam. In this way, a cold plasma beam applicator may be used to scan or apply a cold plasma beam over a surface of the mask, such that only the portions of a patient's skin exposed by the apertures of the mask are treated by the cold plasma beam.

27 Claims, 12 Drawing Sheets

(52) U.S. Cl.
CPC ............... *A61B 2018/00583* (2013.01); *A61B 2018/20355* (2017.05)

(56) References Cited

U.S. PATENT DOCUMENTS

| | | | | |
|---|---|---|---|---|
| 6,413,255 | B1 | 7/2002 | Stern | |
| 6,425,912 | B1 | 7/2002 | Knowlton | |
| 6,438,424 | B1 | 8/2002 | Knowlton | |
| 7,006,874 | B2 | 2/2006 | Knowlton et al. | |
| 7,618,429 | B2 | 11/2009 | Mulholland | |
| 8,475,507 | B2 | 7/2013 | Dewey et al. | |
| 8,652,130 | B2 | 2/2014 | Kreindel | |
| 9,283,029 | B2 | 3/2016 | Britva et al. | |
| 9,545,284 | B2 | 1/2017 | Karni | |
| 9,737,359 | B2 | 8/2017 | Livneh | |
| 10,857,037 | B2 | 12/2020 | Jackson et al. | |
| 2006/0155266 | A1* | 7/2006 | Manstein | A61B 18/203 606/17 |
| 2006/0271028 | A1 | 11/2006 | Altshuler et al. | |
| 2007/0068537 | A1 | 3/2007 | Giovannoli | |
| 2007/0288078 | A1 | 12/2007 | Livneh | |
| 2008/0021442 | A1 | 1/2008 | Manstein et al. | |
| 2008/0287943 | A1 | 11/2008 | Weber et al. | |
| 2009/0318909 | A1 | 12/2009 | DeBenedictis et al. | |
| 2009/0326571 | A1 | 12/2009 | Mulholland | |
| 2010/0023003 | A1 | 1/2010 | Mulholland | |
| 2012/0029499 | A1 | 2/2012 | Bernabei | |
| 2012/0226214 | A1 | 9/2012 | Gurtner et al. | |
| 2013/0072858 | A1* | 3/2013 | Watson | H01J 37/3244 604/23 |
| 2013/0345620 | A1 | 12/2013 | Zemel et al. | |
| 2014/0005644 | A1 | 1/2014 | Karni et al. | |
| 2014/0184072 | A1* | 7/2014 | Jacofsky | A61B 18/042 315/111.21 |
| 2014/0188195 | A1* | 7/2014 | Jacofsky | A61N 5/0616 607/88 |
| 2015/0196359 | A1 | 7/2015 | Paithankar | |
| 2015/0250478 | A1* | 9/2015 | Lam | A61M 13/00 604/23 |
| 2015/0343231 | A1* | 12/2015 | Sanders | A61L 2/14 607/2 |
| 2016/0220802 | A1 | 8/2016 | Haung et al. | |
| 2019/0254734 | A1* | 8/2019 | Konesky | A61B 18/042 |

OTHER PUBLICATIONS

International Search Report and Written Opinion for PCT Application No. PCT/US2018/015418; dated Mar. 23, 2018; fifteen (15) pages.

* cited by examiner

APPARATUS AND METHOD FOR COLD PLASMA SKIN RESURFACING

PRIORITY

This application claims priority to U.S. Provisional Patent Application No. 62/451,337, filed Jan. 27, 2017, entitled "APPARATUS AND METHOD FOR COLD PLASMA SKIN RESURFACING", the contents of which are hereby incorporated by reference in its entirety.

BACKGROUND

Field

The present disclosure relates generally to electrosurgery and electrosurgical systems and apparatuses, and more particularly, to an apparatus and method for cold plasma skin resurfacing.

Description of the Related Art

Skin resurfacing is a process that utilizes the application of energy to the skin of a patient to remove wrinkles, sun damage, age spots, scars, including acne scars, stretchmarks, actinic keratosis, and telangiectasia (e.g., "spider veins"). Skin resurfacing can be broadly divided into ablative and non-ablative skin resurfacing. Ablative skin resurfacing affects the skin to a greater depth, has a prolonged recovery period, but has long lasting effects. Non-ablative skin resurfacing is somewhat more superficial, has a shorter recovery period, but may require periodic retreatment.

Skin resurfacing has become a popular option for patients seeking to treat skin issues. However, using current techniques, patient may be required to endure long recovery times and/or inconsistent results in receiving skin resurfacing treatment. Therefore, a need exists for skin resurfacing techniques that reduce recovery times and provide for more consistent results.

SUMMARY

The present disclosure is directed to a system, apparatus and method for cold plasma skin resurfacing. In one aspect of the present disclosure, a mask for use in fractionated skin resurfacing is provided. The mask includes a plurality of apertures distributed across a surface of the mask. The mask may be made of a flexible material including an adhesive surface, such that, the mask may be applied to a contoured surface of a patient's skin while remaining fixed in place. The material is resistant to the effects of a cold plasma beam. In this way, a cold plasma beam applicator may be used to scan a cold plasma beam over a surface of the mask, such that, only the portions of a patient's skin exposed by the apertures of the mask are treated by the cold plasma beam.

In another aspect of the present disclosure, a method for fractionated skin resurfacing is provided including: providing a mask for skin resurfacing, wherein the mask is made of a non-conductive material; applying the mask to an area of skin of a patient to be treated, the mask including a surface and a plurality of apertures disposed through the surface; and applying a cold plasma beam to the surface of the mask such that the cold plasma beam contacts portions of the area of skin exposed by the plurality of apertures.

In another aspect of the present disclosure, a system for fractionated skin resurfacing is provided including: a mask including a plurality of apertures disposed through a surface, wherein the mask is made of a non-conductive material and configured to be applied to an area of skin of a patient to be treated; and a cold plasma applicator configured to apply a cold plasma beam to the surface of the mask, wherein the cold plasma beam contacts portions of the area of skin exposed by the plurality of apertures.

In another aspect of the present disclosure, a mask for fractionated skin resurfacing is provided including: a surface including a plurality of apertures disposed through the surface, wherein the mask is made of a non-conductive material and configured to be applied to an area of skin of a patient to be treated, such that when a cold plasma beam is applied to the surface of the mask, the cold plasma beam contacts portions of the area of skin exposed by the plurality of apertures.

BRIEF DESCRIPTION OF THE DRAWINGS

The above and other aspects, features, and advantages of the present disclosure will become more apparent in light of the following detailed description when taken in conjunction with the accompanying drawings in which.

Figure 1A:
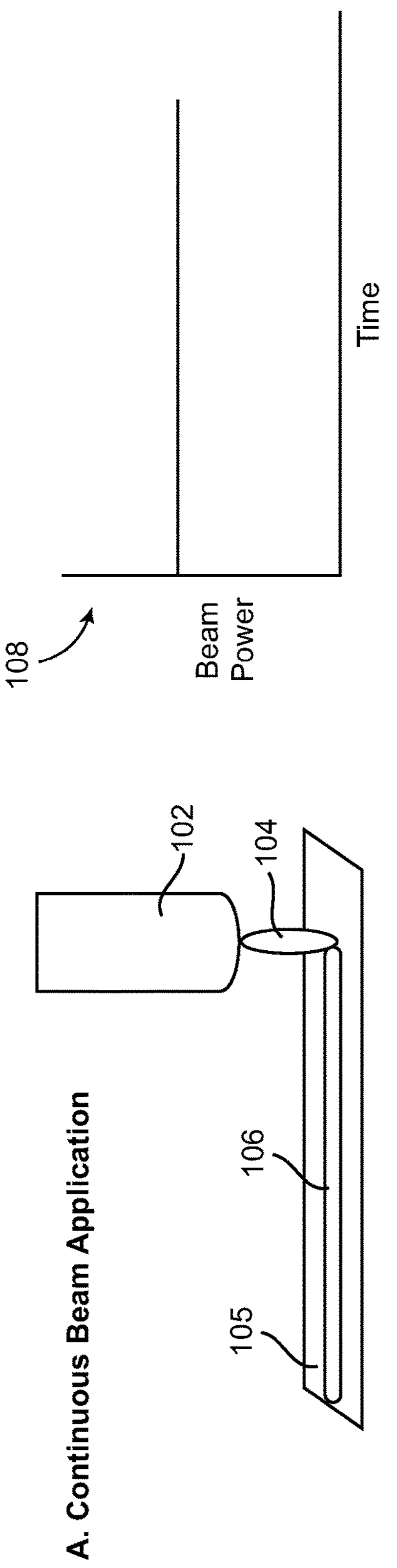
FIG. 1A is an illustration of a cold plasma applicator treating a region of tissue with a continuous beam of plasma in accordance with the present disclosure.

It should be understood that the drawings are for purposes of illustrating the concepts of the disclosure and are not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

The present disclosure is directed to an apparatus and method for skin resurfacing. In one embodiment of the present disclosure, a mask for use in fractionated skin resurfacing is provided. The mask includes a plurality of apertures distributed across a surface of the mask. The mask may be made of a flexible material including an adhesive surface, such that, the mask may be applied to a contoured surface of a patient's skin while remaining fixed in place. In one embodiment, the material is resistant to the effects of a cold plasma beam. In this way, a cold plasma beam applicator may be used to scan a cold plasma beam over a surface of the mask, such that, only the portions of a patient's skin exposed by the apertures of the mask are treated by the cold plasma beam.

Fractionated skin resurfacing can be considered as a hybrid of ablative and non-ablative skin resurfacing. Fractionated skin resurfacing employs small localized regions of ablative skin resurfacing treatment with areas of untreated skin between these regions. This combination provides an overall effect similar to ablative skin resurfacing, but with much shorter recovery times, and comparable durability.

In ablative skin resurfacing, using a laser, for example, sufficient energy density is applied to the skin to cause a peeling of the surface layers. In laser fractional skin resurfacing, the laser is applied to an array of small regions of the skin in comparable energy density to the continuous ablative approach. The laser beam can be focused to a relatively small spot size and rapidly repositioned while being modulated on and off to produce the array pattern of treated areas. The laser beam, while being modulated, can scan in a raster pattern, a random "flying spot" approach, or other scan patterns to treat a given region. The laser applicator is then moved to a new region, and the process is repeated. An illuminated optical guide projection may be used in conjunction with the laser scanner to align treated and untreated regions.

In one embodiment of the present disclosure, a cold plasma applicator may be used for skin resurfacing. The cold plasma applicator may be used for ablative, non-ablative, and/or fractionated skin resurfacing procedures.

Cold plasma applicators can broadly be classified as a local discharge, or non-attached discharge type and direct discharge, or attached discharge type. In the local, or non-attached discharge cold plasma applicators, the plasma discharge is confined to the applicator, and may employ a ground ring or similar structure at the applicator exit nozzle. The cold plasma beam primarily consists of afterglow plasma effects, heated carrier gas, and long-lived radical species produced by the interaction of the plasma beam and the surrounding air. It should be noted that the term "cold" in cold plasma refers to the degree of ionization of the carrier gas, and the overall temperature of the carrier gas may well be in excess of 100 degrees centigrade. In contrast to thermal plasma, during the generation of cold plasma, only a small fraction of the atoms of the carrier gas are ionized. Examples of carrier gases include inert gases, such as, helium or argon, or nitrogen which, at typical application temperatures, are still chemically inert.

In a direct, or attached discharge cold plasma applicator, a continuous discharge path exists from the applicator to the target surface, e.g., a patient's skin. The target surface, which must necessarily be reasonably electrically conductive, acts as a second electrode comparable to the nozzle ring electrode of the local discharge applicator. The direct discharge cold plasma applicator deposits energy onto the target surface through both heated carrier gas and through direct (attached) contact electrical discharge of the plasma beam with the target surface. Both long-lived and short-lived radical species are present at the application surface.

Figure 1B:
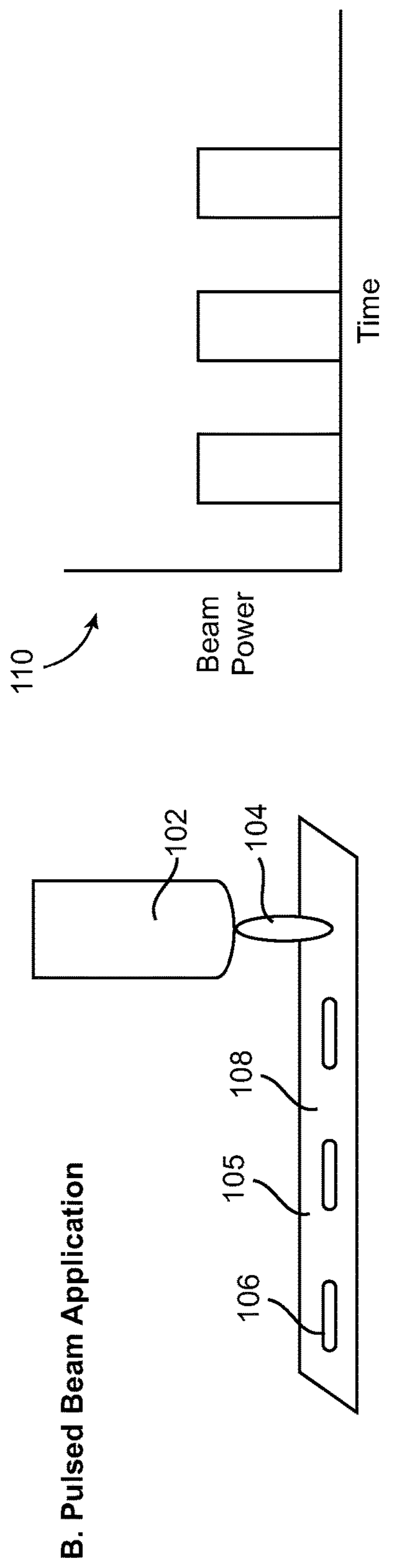
FIG. 1B is an illustration of a cold plasma applicator treating a region of tissue with a pulsed beam of plasma in accordance with the present disclosure.

Cold plasma applicators, particularly of the direct discharge type, can produce a fractionation effect by either modulating the plasma beam, both spatially and temporally, or by using a mask. Referring to FIG. 1A, a cold plasma applicator 102 is shown using spatial modulation to produce a fractionation effect in accordance with the present disclosure. As seen in FIG. 1A, cold plasma applicator 102 produces a plasma beam 104. The plasma beam 104 is applied to a treated region 106 of the skin or tissue 105 of a patient while scanning the region 106 (e.g., side to side). In the embodiment of FIG. 1A, the beam 104 is continuously applied while maintaining the power of the plasma beam 104 at a predetermined level. The continuous beam application (i.e., constant power) is shown in graph 108 of FIG. 1A. Referring to FIG. 1B, cold plasma applicator 102 is shown using temporal modulation to produce a fractionation effect in accordance with the present disclosure. In the embodiment, shown in FIG. 1B, power of the plasma beam 104 is modulated or pulsed periodically, as shown in graph 110. When the beam 104 is pulsed, a series of treated regions 106 are produced on the skin or tissue 105 of the patient, interspersed by untreated regions 108. An example of a plasma generator or applicator capable of producing a modulated or pulsed plasma beam is described in commonly owned U.S. Pat. No. 9,649,143, the contents of which are hereby incorporated by reference.

Although spatial and temporal modulation of plasma beam 104 may be used in skin resurfacing procedures as shown in FIGS. 1A and 1B, several disadvantages to these techniques exist. For example, inadvertent variations in the scanning speed of the applicator 102 will produce similar variations in the location and duration of treated and untreated areas. There is also a potential difficulty in aligning subsequent scan lines so that the treated and untreated areas of adjacent scan lines are optimally positioned.

Figure 2B:
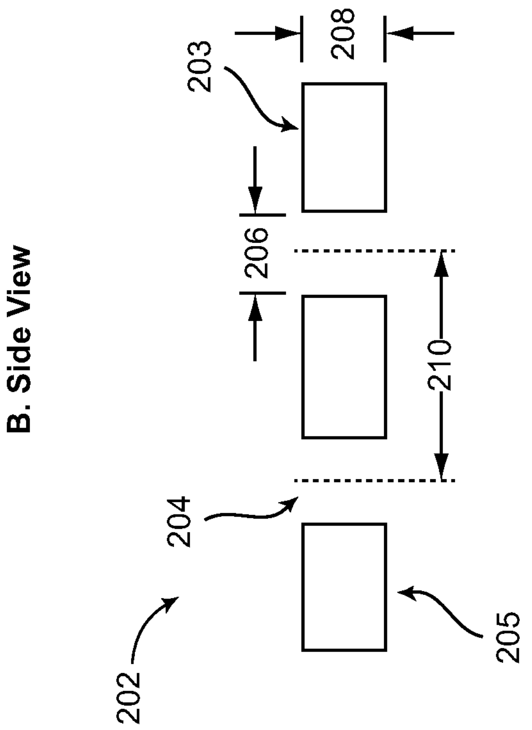
FIG. 2B is a side view of the mask of FIG. 2A in accordance with the present disclosure.
Figure 2A:
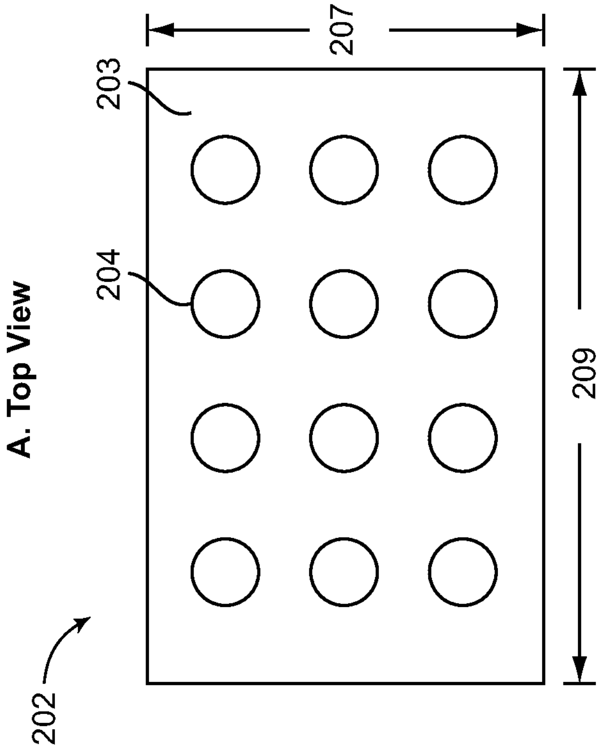
FIG. 2A is a top view of a mask for use in fractionated skin resurfacing in accordance with the present disclosure.

An alternate approach to achieve cold plasma fractionation is to use a fractionation mask. Referring to FIGS. 2A and 2B, a top view is shown in FIG. 2A and a side view cross-sectional view is shown in FIG. 2B of a fractionation mask 202 in accordance with the present disclosure. As will be described below, the fractionation mask 202 is configured to be used with a cold plasma applicator, such as applicator 102, to perform fractionated skin resurfacing on the skin of a patient.

As seen in FIGS. 2A and 2B, the mask 202 includes a top surface 203 and a bottom surface 205. The mask 202 is configured to be flexible, such that, the mask 202 is conformal to the skin surface to be treated. Furthermore, the bottom surface 205 may include an adhesive backing. In this way, bottom surface 205 may be applied to a desired skin surface, such that, the mask 202 may conform to any curves in the skin surface and be held in place by the adhesive backing. Additionally, the mask 202 includes a plurality of apertures 204 extending from the top surface 203 to the bottom surface 205. Each aperture 204 has a predetermined mask aperture or hole diameter 206 and a predetermined mask aperture or hole spacing 210 from adjacent apertures 204. Furthermore, the mask 202 has a predetermined thickness 208.

The mask 202 may be constructed of a non-conductive material that is resistant to the cold plasma beam 104 and also has sufficient dielectric strength such that the beam voltage will not cause the material to electrically break down in regions between the apertures 204. Generally, any plastic material may be used such as the typical plastics used in medical applications such as, but not limited to, polyethylene, polypropylene, polystyrene, polyester, polycarbonate, PVC, polysulfone, polyether ether ketone (PEEK), etc. In this way, when beam 104 is applied by applicator 102 over mask 202, beam 104 is only allowed to pass through apertures 204 to the skin of the patient.

It is to be appreciated that the diameter 206 and spacing 210 of the apertures 204 and mask thickness 208 may be optimized to achieve a desired effect for a given cold plasma power setting, carrier gas flow rate, and applicator scan speed. In some embodiments, the diameter 206, spacing 210 of apertures 204 and mask thickness 208 are selected based on the beam diameter of the plasma beam 104 that will be applied to the mask 202.

For example, in one embodiment, for a skin resurfacing procedure, the aperture diameter 206 is at least equal to, or greater than the beam diameter of beam 104 which, depending on the power setting, may be between 1 and 2 mm. The spacing 210 between apertures 204 is generally at least 1 beam diameter. The mask thickness 208 is limited by a cooling gas flow shadowing effect from the aperture walls. The plasma beam 104 itself consists of an inner core of plasma discharge, surrounded by sheath of un-ionized cooling gas flow. If the mask 202 is too thick, the associated cooling effect of the un-ionized beam sheath gas flow is reduced through interaction with the aperture walls of the mask 202. This results in excessive heating in this region and may produce undesirable tissue effects in proximity to the walls. To prevent this, in one embodiment, the mask thickness 208 is at least one half the beam diameter, and preferably, one tenth the beam diameter. The lower limit on mask thickness 208 is dictated by mask material considerations, such as mechanical strength and ability to withstand the effects of the plasma beam 104. The upper limit of aperture diameter 206 and spacing 210 is largely determined by a tradeoff of enhanced recovery time versus achieving the desired physiological effect. As a practical consideration, if the aperture 204 is substantially larger than ten beam diameters, the local tissue effect is the same as if no mask were used. Similarly, if the spacing 210 between apertures 204 is substantially greater than ten beam diameters, the overall physiological effect is reduced and may not achieve the desired resurfacing outcome.

Additionally, there are different considerations related to skin thickness which varies per region to be treated. Skin thickness differences may result in differences in optimizing the treated vs. non-treated tissue mentioned above.

In practice, the bottom surface 205 of mask 202 is applied to the region of skin to be treated, and the cold plasma applicator 102 is scanned across the top surface 203 of the mask 202. The cold plasma beam 104 enters a given aperture 204 as the applicator 102 passes over the given aperture 204 and the beam 104 contacts the skin at this location. The remainder of the mask 202 (e.g., the portions not including apertures 204) deflects the cold plasma beam 104, producing untreated areas between the apertures 204. The mask 202 is then removed, revealing a cold plasma fractionated skin resurfacing, i.e., small localized regions affected by the cold plasma beam with areas of untreated skin between and surrounding these regions. In this manner, healing may occur in the affected localized regions, not only by the underlying tissue, but assisted by the surrounding untreated areas resulting in shorter recovery times.

It is to be appreciated that depending on the material chosen, the mask 202 may be configured to be scanned as many times as necessary to get the desired effect without effecting the integrity of the mask 202. The rate of scanning the cold plasma beam 104 over the mask 202 is not controlled. This is one of the benefits of the mask (i.e. controlling scanning is not as critical). The skin is only treated through the apertures 204 and does not rely on the hand of an operator. In this way, the mask 202 provides a larger factor of safety.

In one embodiment, mask 202 may be configured as a plurality of strips of any desired shape (e.g., rectangular, circular, etc.) to be applied to one or more areas of a patient's skin.

It is to be appreciated that the mask 202 may be configured to be used on any skin surface of a patient. For example, the length 207 and width 209 of the mask may be chosen to accommodate larger or smaller surfaces areas of skin.

In another embodiment, the mask 202 is made of a material that retains cold temperatures (i.e., temperatures below the ambient temperature or temperature of the surrounding environment) for extended periods of time such as, but not limited to, hydroxyethyl cellulose, sodium polyacrylate, or vinyl-coated silica gel such as those used in gel packs for treating sports injuries, etc. Mask 202 may be refrigerated prior to application to the tissue of the patient to lower the temperature of mask 202 and keep the epidermal tissues of the patient cool during the treatment.

For example, the temperature of mask 202 may be lowered (e.g., via refrigeration or other means) so the surface 205 of the mask 202 contacting the patient's skin is below a predetermined temperature setpoint, e.g., 45 degrees Fahrenheit. Other temperature setpoints are contemplated to be within the scope of the present disclosure. In one embodiment, the mask 202 is chilled to a temperature at least lower than a surface temperature of the skin or tissue surface the mask 202 is to be applied to. The surface temperature of the skin the mask 202 is to be applied to may be determined by measuring the surface temperature of the skin with a temperature sensor before performing the skin resurfacing procedure. Alternatively, the surface temperature of the skin may be determined or estimated based on a normal average surface skin temperature (where the average is determined in normal ambient temperature settings) determined empirically. In one embodiment, the normal average surface skin temperature is between 90 and 97 degrees Fahrenheit and the mask 202 is chilled to at least below 90 degrees Fahrenheit.

In one embodiment, the mask 202 may consist of multiple layers, each having different heat transfer properties to keep the epidermal tissue of the patient cool during treatment. For example, referring to FIG. 2C, mask 202 is shown including a first layer 230 and a second layer 232 in accordance with the present disclosure. The side or surface 203 of mask 202 that faces away from the patient's skin or tissue is made of a first layer of material 230 and the side or surface or surface 205 that face toward the patient's skin or tissue is made of a second layer of material 232. It is to be appreciated, as stated above, surface 205 may be configured with adhesive backing to adhere to the skin of the patient after being applied. The first layer 230 is made of a thermally insulating material. The second layer 232 is made of a material that retains cold temperatures (i.e., temperatures below the ambient temperature) for extended periods of time (such as any of the materials described above). Layers 230 and 232 are configured to provide a more effective cooling effect to the epidermal tissue of the patient. Layer 230 insulates layer 232 from the environment surrounding mask 202, such that heat only flows from the tissue of the patient to mask 202 and not from mask 202 to the surrounding environment. In this way, layer 232 retains lower or cooler temperatures more effectively for extended periods of time because the absorption of heat from the surrounding environment is reduced and thus the temperature increase of layer 232 due to the surrounding environment is reduced.

Figure 2C:
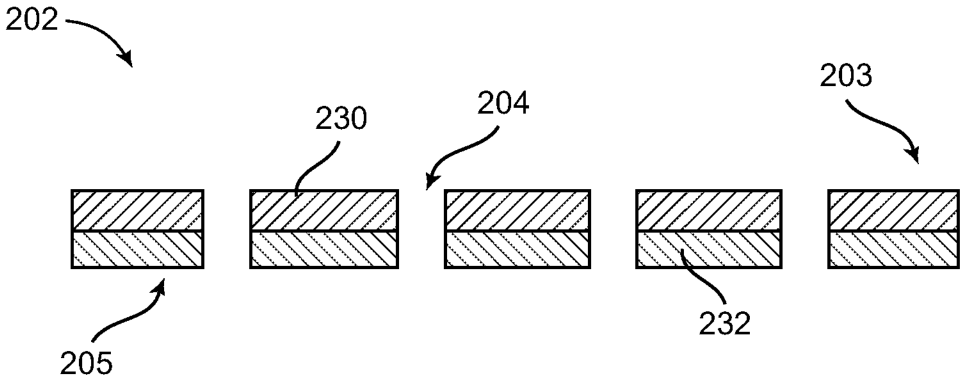
FIG. 2C is a cross section view of a mask including multiple layers in accordance with the present disclosure.
Figure 2D:
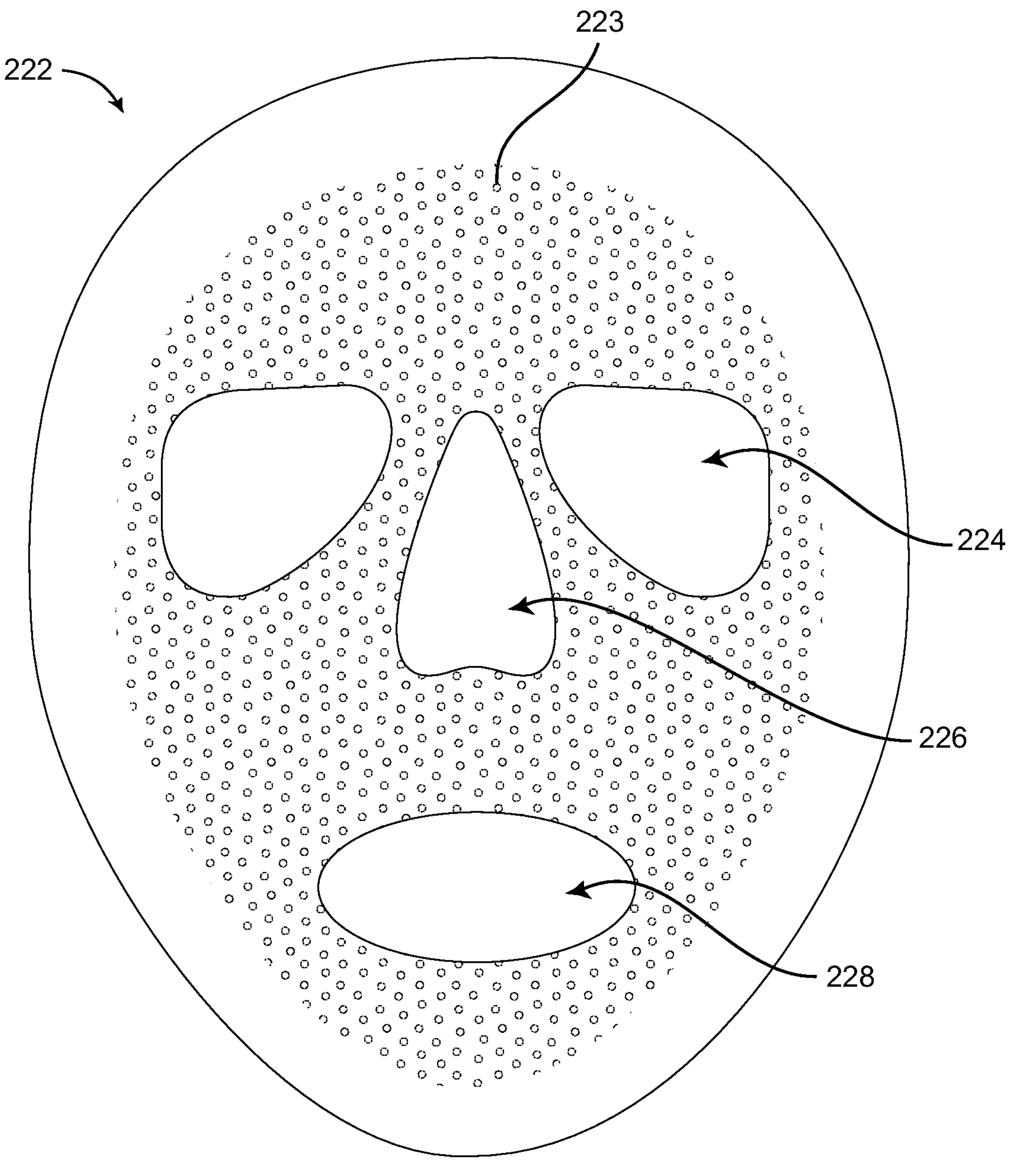
FIG. 2D is a top view of a mask configured to be applied to a face of a patient in accordance with the present disclosure.

Additionally, the mask 202 could be shaped and modified to accommodate different parts of a patient's body. For example, referring to FIG. 2D, a top view of mask 222 is shown in accordance with the present disclosure, where mask 222 has been configured to be applied to a patient's face. As seen in FIG. 2D, the mask 222 may be shaped to substantially cover the face of a patient including a plurality of apertures 223. Furthermore, the mask 222 may include apertures 224, 226, 228 for the eyes, nose and mouth of the patient, respectively. In one embodiment, the patient's face may be scanned, for example, by a three-dimensional imaging device so that the mask 222 may be tailored exactly for the dimensions of the patient's face.

Figure 2E:
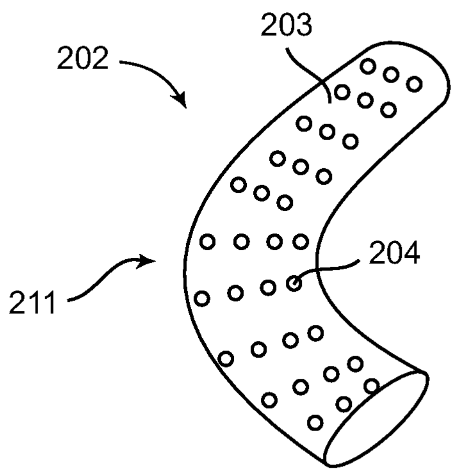
FIG. 2E illustrates a mask configured as a sleeve in accordance with the present disclosure.
Figure 2F:
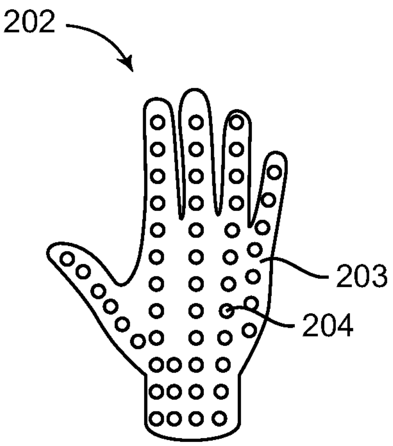
FIG. 2F illustrates a mask configured as a glove in accordance with the present disclosure.
Figure 2G:
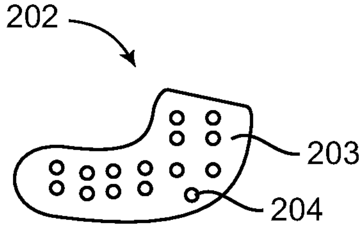
FIG. 2G illustrates a mask configured as a boot in accordance with the present disclosure.

Although the mask is shown in FIG. 2D as being configured to be applied to a patient's face, the mask 202 may be configured to be applied to other parts of the patient's body as desired. For example, the mask 202 may be configured to be applied to the patients, feet, hands, chest, etc. Referring to FIG. 2E, in one embodiment, the mask 202, including apertures 204 in surface 203, may be configured as a sleeve to be applied over an arm or leg of a patient. The sleeve may include a bend 211 to accommodate joints of the patient (e.g., a knee or elbow). Referring to FIGS. 2F and 2G, in another embodiment, the mask 202 may be configured as a glove or a boot to be applied over a hand or foot of a patient. It is to be appreciated that different power levels of the cold plasma beam may be employed depending on what area of the body is being treated. For example, if the mask is applied to other parts of the body, such as the neck, a lower power level may be needed to prevent excessive recovery times. Conversely, applying the mask to the legs for spider vein removal may require higher power levels.

Referring again to FIG. 2A, although apertures 204 of mask 202 are shown evenly distributed across the area of surface 203, in other embodiments, the spacing 210 of the apertures 204 may vary for different portions of surface 203 to achieve different intensity levels for the skin resurfacing treatment on certain areas of a patient's skin. For example, the apertures 204 may be very tightly spaced across one portion of mask surface 203 (i.e., the mask hole spacing 210 may be less than a predetermined value or distance) and less tightly spaced across another portion of mask surface 203 (i.e., the mask hole spacing 210 may be greater than a predetermined value or distance) to adjust the amount of plasma per unit area that is applied to different portions of a patient's skin. In another embodiment, the diameters 206 of the apertures 204 may be adjusted in different portions of the mask 202 to achieve different intensity levels or plasma per unit area for the skin resurfacing treatment on certain areas of a patient's skin.

Figure 3:
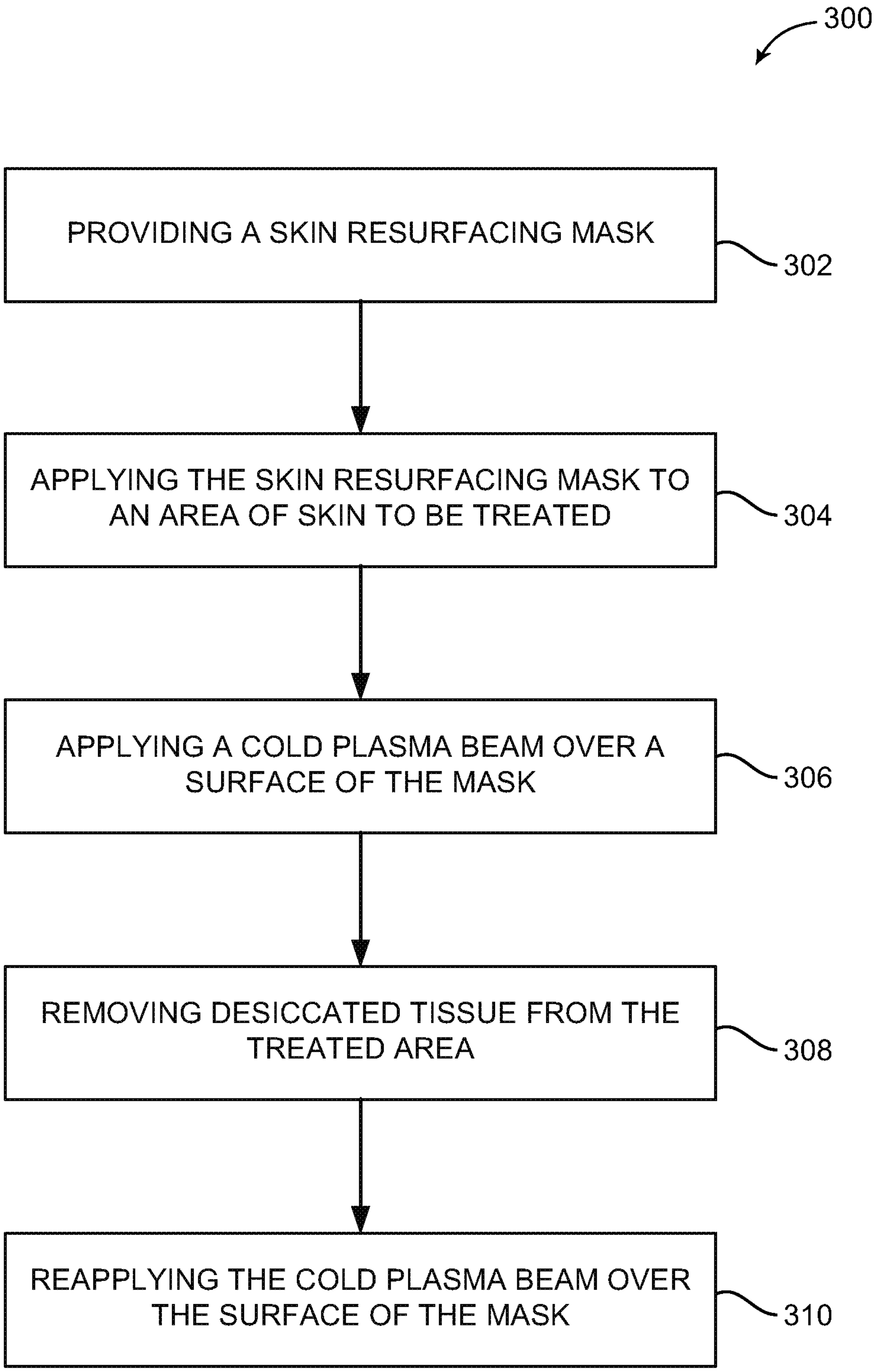
FIG. 3 is a flow chart of a method for performing cold plasma skin resurfacing on a patient using a mask in accordance with the present disclosure.

Referring to FIG. 3, a flow chart of a method 300 for using mask 202 (or any other mask described above or below) for fractionated skin resurfacing is shown in accordance with the present disclosure. In step, 302, a skin resurfacing mask 202 is provided. As stated above, the mask 202 may be configured for use with a particular part of the body of the patient (e.g., the patient's face, as shown in FIG. 2C). In step 304, the skin resurfacing mask 202 is applied to skin to be treated. In step 306, a cold plasma beam is applied over the surface of the mask 202 facing away from the patient (i.e., surface 203). For example, a cold plasma beam applicator 102 may be used to scan a plasma beam 104 on surface 203 of mask 202, where the plasma beam 104 only passes through the apertures 204 of the mask and, therefore, only treats the areas of skin exposed by the apertures 204.

It is to be appreciated that the scanning of the plasma beam over the mask may be repeated, e.g., at least two passes. In one embodiment, one pass of the plasma beam is applied, as in step 306, followed by removal of the desiccated tissue by applying saline to the treated skin, in step 308. In one embodiment, the applying the saline to the treated skin of step 308 further includes wiping the treated skin with a saline soaked gauze pad. Then, a second pass is applied, in step 310. In certain embodiments, a predetermined cooling period may be implemented between the initial application of step 306 and subsequent applications as in step 310. In other embodiments, there is enough of a delay between passes, because the second pass may be started at the same point on the mask 202 as the starting point of the first pass. Therefore, by the time the first pass has ended and the second pass is about to begin, the tissue treated at the beginning of the first pass has had time to cool.

It is further to be appreciated that the present disclosure contemplates procedures where one, two or more passes are implemented. After each pass of the cold plasma beam, the treated area is to be wiped with a saline soaked gauze pad to remove the desiccated tissue prior to the next pass. In one embodiment, the holes or apertures 204 of the mask 202 are sufficiently sized to enable the saline to reach the treated skin or tissue. In other embodiments, the mask 202 may be removed before wiping the treated skin. In this embodiment, the mask 202 needs to be realigned on the tissue before the second pass so the same specific points on the treated skin are accessed. In one embodiment, the mask 202 may include at least two additional apertures employed to align the mask. Before the first pass of cold plasma, a user may mark the skin to be treated, e.g., with a marker, through the at least two additional apertures. When applying the cold plasma beam on the first pass, the user may avoid these additional apertures. After removing the mask 202 to wipe the treated skin, the mask 202 may be aligned by aligning the additional apertures with the marked portion of the treated skin.

In one embodiment of the present disclosure, mask 202 may be configured as a hand-held card as an alternative method to including an adhesive backing. In this embodiment, an edge or corner of mask 202 may be configured to be held by a user during a procedure, such that mask 202 can be placed on (i.e., in contact with), or proximately to (i.e., just above), an area of skin to be treated as desired by the user. In this way, a user may move the hand-held card-type mask to any part of the patient's body as desired to perform skin resurfacing using cold plasma and mask 202 in the manner described above. In one embodiment, the hand-held card-type mask includes a handle extending from an edge or corner of mask 202 and configured to be gripped by a user, such that the user's hand may be further away from the mask 202 and the treatment area while mask 202 is in use. In some embodiments, the handle may extend at an acute angle relative to surface 203 of mask 202 to aid placement of mask 202 on a surface to be treated.

In some embodiments, the hand-held card-type mask 202 may be configured in predefined shapes to support various procedures relating to different portions of a patient's body. For example, the hand-held card-type mask 202 may be configured in the shape of a patient's eye to be placed over or on a patient' eye to perform skin resurfacing on a patient's eye lid. It is to be appreciated that the hand-held card-type mask 202 may be configured in other shapes as well, such as, but not limited to, shapes resembling a patient's chin, cheek, neck, etc. In some embodiments, predetermined portions of the hand-held card-type mask 202 may be configured without apertures to protect sensitive regions of a user's body (e.g., lips, eyes, nose, etc.) when skin area proximate to the sensitive regions are treated.

In another embodiment, the card-type mask may be configured to facilitate treatment around one or more body structures (e.g., the eyes or nose) of a patient. For example, referring to FIG. 4A, hand-held card-type masks 402 and 450 are shown in accordance with the present disclosure. It is to be appreciated that masks 402 and 450 may be made of any of the suitable materials and include any of the features described above in relation to mask 202.

Figure 4A:
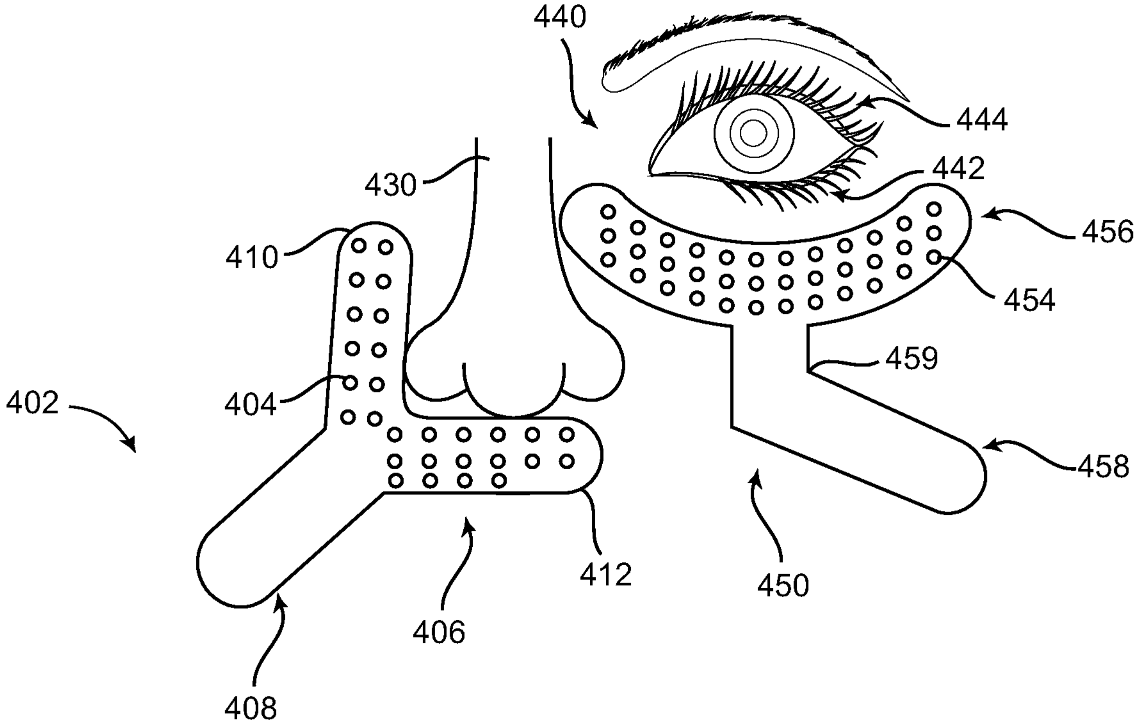
FIG. 4A illustrates first and second hand-held card-type masks in accordance with the present disclosure.

Mask 402 includes a handle portion 408 configured to be gripped by a user, and a portion 406 shaped for performing the skin resurfacing procedure described above for the area surrounding a patient's nose 430. Portion 406 includes first and second extension members 410, 412, which each include a plurality of apertures 404. Extension members 410, 412 extend from hand portion 408 at an angle relative to each other. In this way, as shown in FIG. 4A, when mask 402 is placed proximately to a patient's nose 430, a first extension member (e.g., extension member 410) is disposed over the skin adjacent to the patient's nose 430 associated with the patient's cheek, and a second extension member (e.g., extension member 412) is disposed over the skin beneath the patient's nose 430 (e.g., between the patient's nose 430 and upper lip). In use, the mask 408 may be manipulated and positioned as desired about the patient's nose 430 and the skin adjacent to the patient's nose 430 may be treated by applying a cold plasma beam, using one or more passes, over extensions members 410, 412.

Mask 450 includes a handle portion 458 configured to be gripped by a user, and a portion 456 shaped for performing the skin resurfacing procedure described above for the upper and lower eye lids 444, 442 surrounding a patient's eye 440. In one embodiment, portion 456 is curved to match the curved outline of a patient's eye. Portion 456 includes a plurality of apertures 454. In use, mask 450 is placed proximately to a patient's eye 440 such that portion 456 is disposed over the upper eye lid 444 or lower eye lid 442 of a patient. In this way, upper eye lid 444 or lower eye lid 442 may be treated by applying a cold plasma beam, using one or more passes, over portion 454. In one embodiment, handle portion 458 may include a bend 459, such that handle portion 458 extends away from portion 456 at an angle. Bend 459 is configured to enable mask 450 to be used without handle portion 458 being obstructed by irregular protrusions of the patient's face (e.g., the patient's nose 430).

It is to be appreciated that although masks 402, 450 are shaped for treating the areas around the nose 430 and eyes 440 of a patient, in accordance with the teaching of the present disclosure, other hand-held card-type masks may be used, which are shaped for treating the areas around other body structures of the patient (e.g., around the lips or ears of a patient).

Figure 4B:
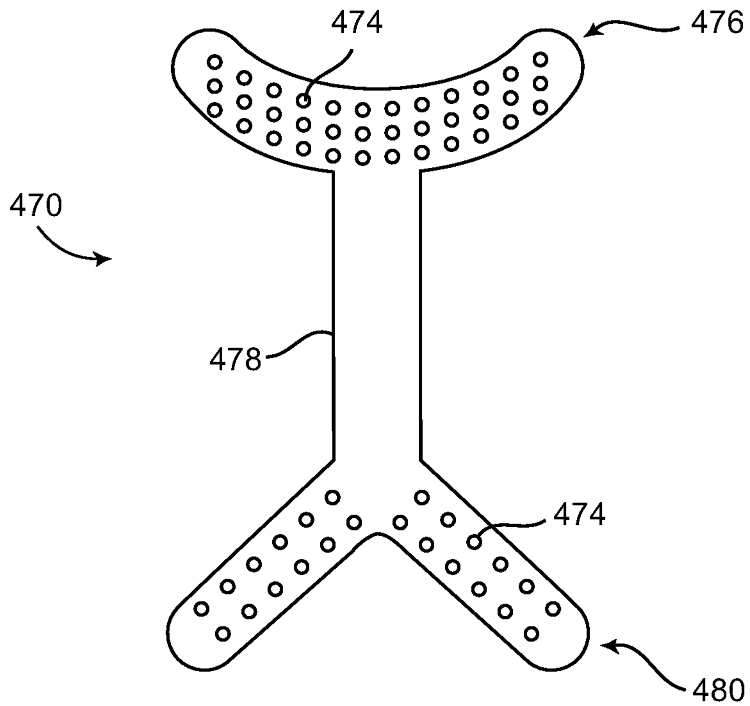
FIG. 4B illustrates another hand-held card-type mask in accordance with the present disclosure.

In one embodiment, a hand-held card-type mask may be configured with multiple shapes to treat the areas around multiple body structures. For example, referring to FIG. 4B, mask 470 is shown in accordance with the present disclosure. Mask 470 includes a first portion 476, a second portion 478, and a third portion 480. Portion 476 is shaped to facilitate treatment of the areas around a user's eye (e.g., the upper or lower eye lids 444, 442 shown in FIG. 4A) and portion 480 is shaped to facilitate treatment of the areas around a user's nose (e.g., as shown in FIG. 4A). Portions 470, 480 include a plurality of apertures 474. Portions 470, 480 are disposed at opposite ends of portion 478, which is configured as a handle to be gripped by a user. In use, mask 470 may be gripped via handle portion 478 and rotated by a user to treat the areas surrounding either the nose or eye of a patient as desired.

In another embodiment of the present disclosure, mask 202 may be configured without apertures 204. In this embodiment, after masks 202 is applied to a user's skin, a microneedling apparatus, such as a microneedle roller, may be used to puncture holes or apertures through the mask 202 and/or the user's skin.

Figure 5A:
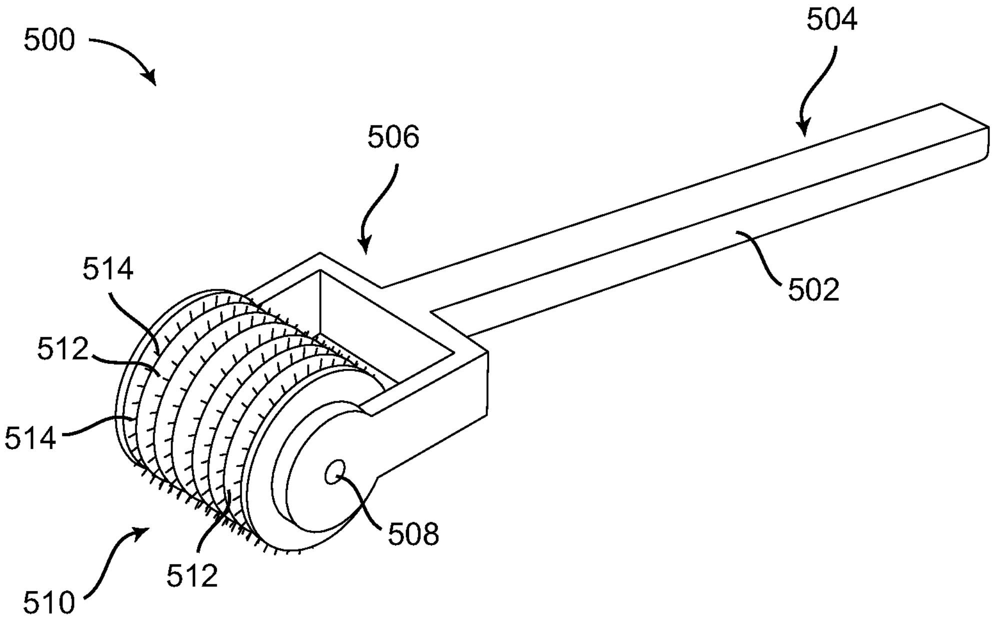
FIG. 5A illustrates a microneedling apparatus in accordance with the present disclosure.
Figure 5B:
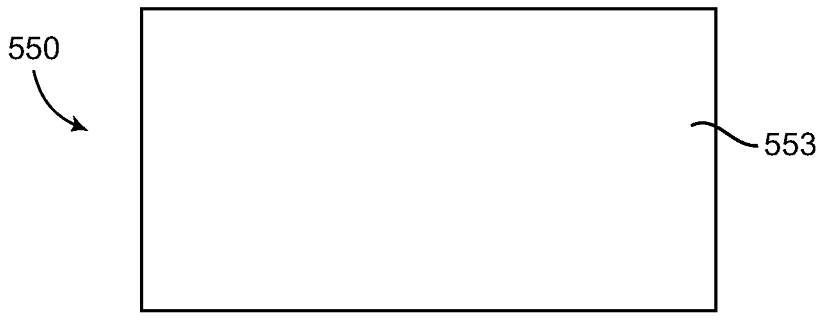
FIG. 5B illustrates a mask without apertures in accordance with the present disclosure.

For example, referring to FIG. 5A, a perspective view of microneedle roller 500 is shown in accordance with the present disclosure. Microneedle roller 500 includes a handle 504 having a portion 502 configured to be gripped by a user and a portion 506 configured to be coupled to a cylindrical roller unit 510. The cylindrical roller unit 510 includes a plurality of disks 512, each including a plurality of microneedles 514 extending from the circumference of each disk 512. Cylindrical roller unit 510 is rotatably coupled to portion 506 via an axis or pin shaft 508, such that unit 510 may be rolled over a surface of a mask. For example, referring to FIG. 5B, a mask 550 is shown in accordance with the present disclosure. Mask 550 may be made of any of the suitable materials described above in relation to mask 202. Mask 550 includes a surface 553. Although not shown, mask 550 also includes a surface opposite to surface 553. The surface opposite to surface 553 may include an adhesive backing for applying the mask 550 to the skin of a patient. As shown in FIG. 5B, surface 553 of mask 550 does not include any apertures.

Figure 5C:
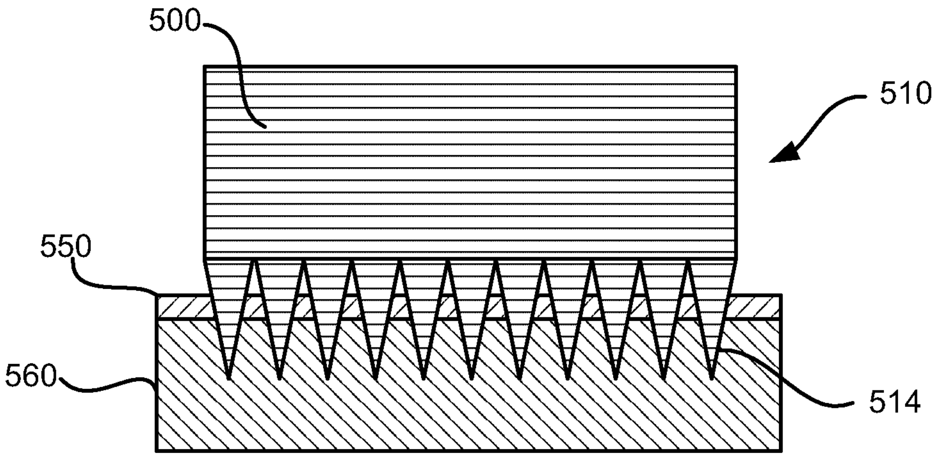
FIG. 5C is a cross-section view of the microneedling apparatus of FIG. 5A be applied over the mask of FIG. 5B and the tissue of a patient in accordance with the present disclosure.
Figure 5D:
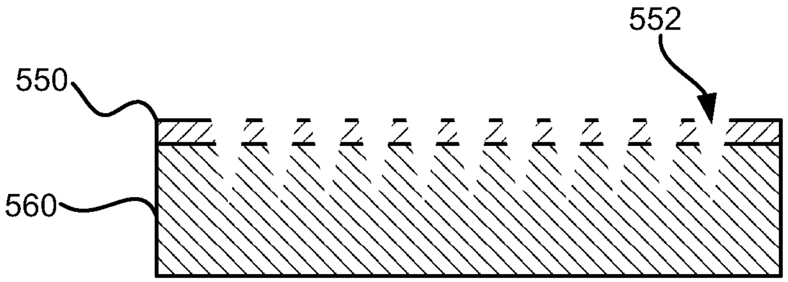
FIG. 5D is a cross-section view of the mask of FIG. 5B and the tissue of the patient after the microneedling apparatus of FIG. 5A has been applied over the mask of FIG. 5B in accordance with the present disclosure.

Referring to FIG. 5C, a cross-section view of roller 500 and mask 550 is shown in accordance with the present disclosure. In use, mask 550 is applied to the skin or tissue 560 of a patient and the cylindrical roller unit 510 of roller 500 is rolled over mask 550, such that pins 514 puncture mask 550 and/or tissue 560. Referring to FIG. 5D, when roller 550 is removed from mask 550 and tissue 560, apertures 552, created by pins 514 of roller 500, are left behind extending through mask 550 and tissue 560. It is to be appreciated that, since mask 550 includes an adhesive backing that adheres mask 550 to skin or tissue 560 of the patient, the plurality of apertures created in mask 550 and the plurality of apertures created in tissue 560 (i.e., where the aperture created in the mask 550 and the aperture created in the tissue 560 together form aperture 552), align. After apertures 552 have been created in mask 550 and tissue 560, a cold plasma beam may be applied over mask 550, using one or more passes, to treat the tissue 560 of the patient. In one embodiment, since apertures 552 extend both through the mask 550 and the tissue 560 of the patient, the cold plasma beam applied to mask 550 penetrates below the surface of the tissue 560 and a more effective skin resurfacing treatment is realized.

It is to be appreciated that the number, density, spacing and diameter of the apertures 552 created by roller 500 being applied over mask 550 and tissue 560 may be configured using roller 500. For example, for an increased number and density of apertures 552, roller 500 may be applied over mask 550 and tissue 560 multiple times and rolled from different angles to create more apertures 552. In another embodiment, roller 500 may include multiple different roller units 510, each with pins of different diameter and spacing based on a desired density, spacing, and diameter to be included in apertures 552. The different roller units 510 may be replaceably mounted to handle 504 and applied to mask 550 and tissue 560 to achieve the desired density, spacing, and diameter for apertures 552 as desired.

Figure 6A:
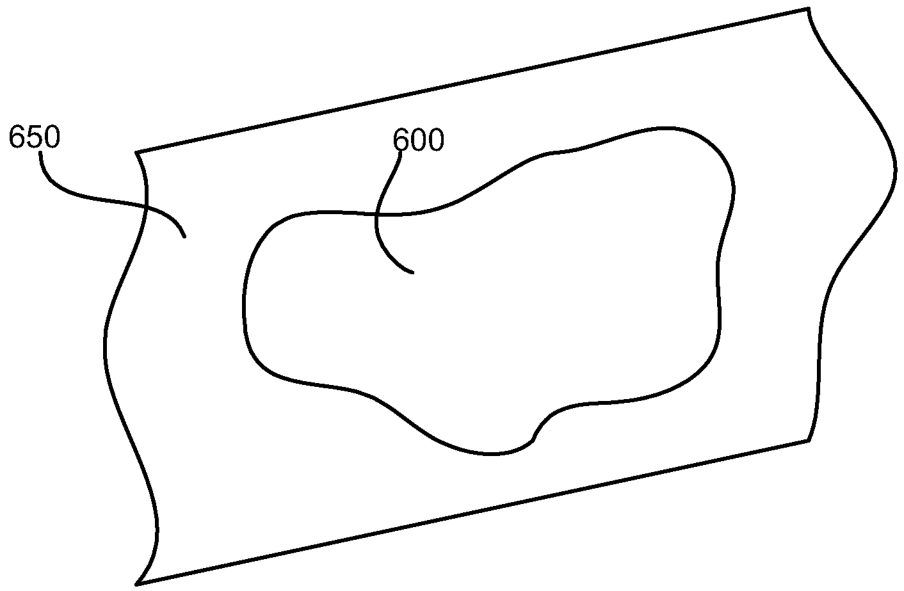
FIG. 6A illustrates a fluid solidifying as a mask over the tissue of a patient in accordance with the present disclosure.
Figure 6B:
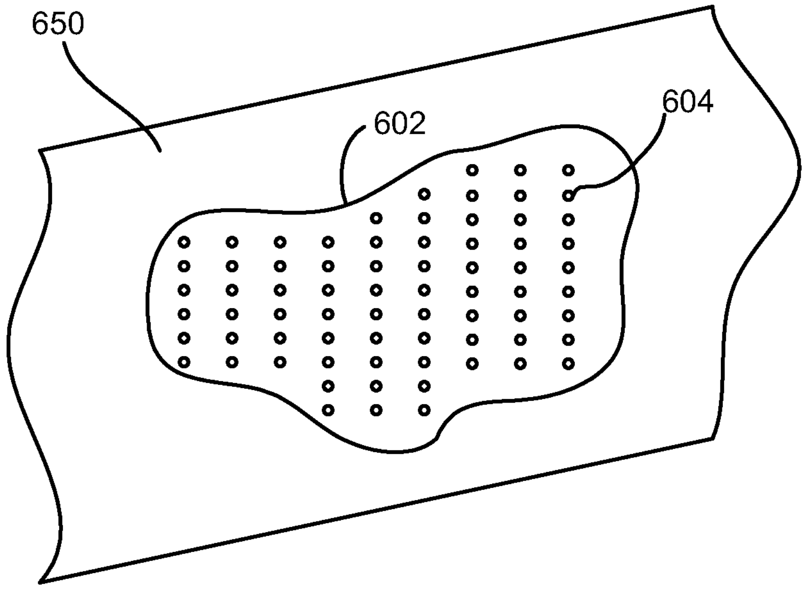
FIG. 6B illustrates the solidified as a mask over the tissue of a patient after a microneedling apparatus has been applied over the solidified mask.

In another embodiment of the present disclosure, a mask in accordance with the present disclosure may be created using a fluid that is applied to a patient skin or tissue 560. In one embodiment, the fluid may be applied to the patient's skin or tissue 560, using a pressurized spray can or other fluid applying apparatus (e.g., a spray gun). In another embodiment, the fluid may be configured as a cream and applied to the patient's skin or tissue 560. In either case, the fluid is configured to solidify or harden into a solid mask after being applied to the patient's skin or tissue 560. After the fluid solidifies into a mask, the mask and skin or tissue 560 may be punctured by a microneedling apparatus, such as, microneedle roller 500 to create apertures in mask and tissue. For example, referring to FIG. 6A, a fluid 600 is shown that has been applied to tissue 650 of a patient. After a predetermined period of time after fluid 600 has been applied, fluid 600 is configured to solidify into a mask. Referring to FIG. 6B, fluid 600 is shown after having solidified into a mask 602. After solidifying into a mask 602, a microneedling apparatus, such as roller 500, is applied one or more times of solidified mask 602 to create apertures 604 through mask 602 and tissue 650.

It is to be appreciated that, as used herein, the word "mask" refers to any material that can be applied directly on, or in close proximity to, a skin or tissue surface to be treated during a skin resurfacing procedure performed in accordance with the principles of the present disclosure. The mask may be made from any of the materials disclosed herein or other suitable materials configured to support the skin resurfacing procedures (including the application of cold plasma to the mask) of the present disclosure.

Figure 7:
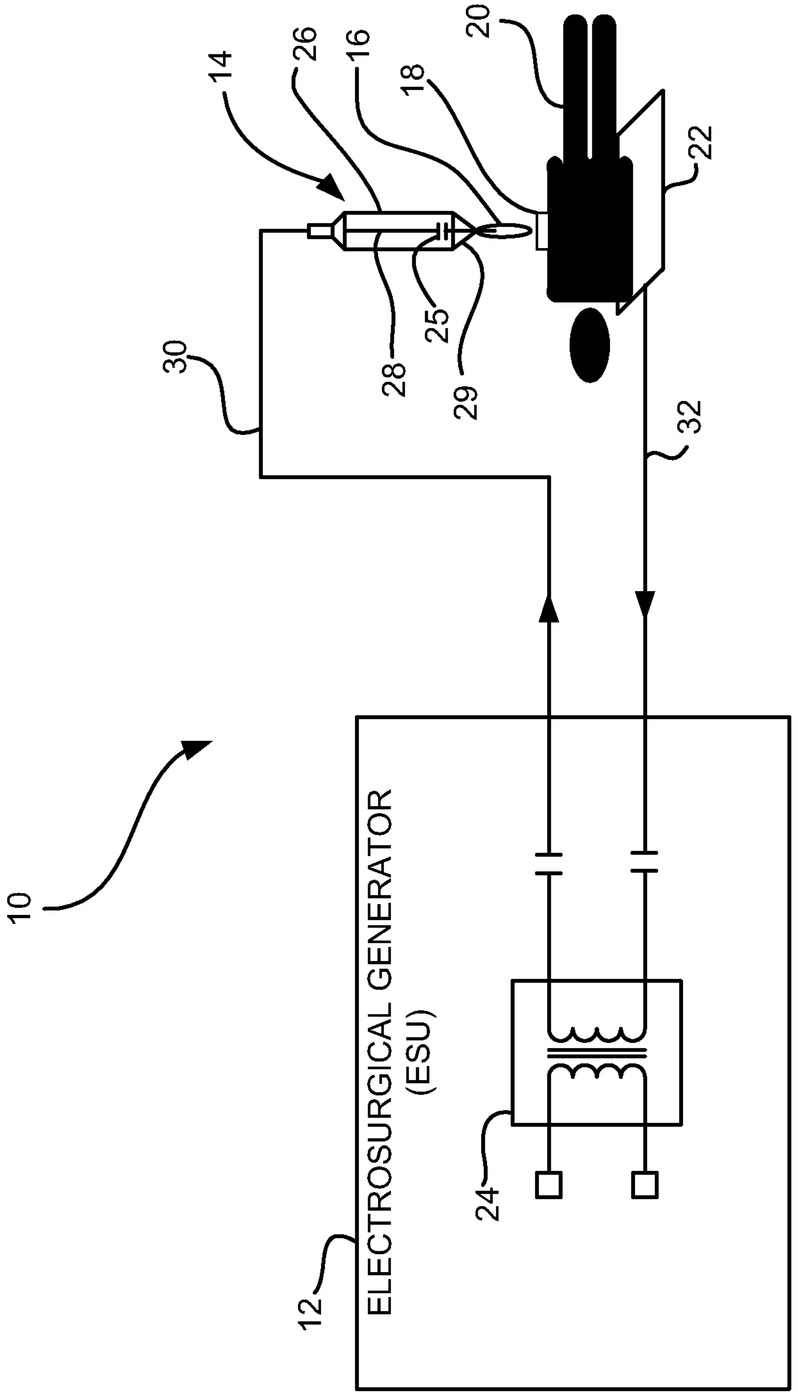
FIG. 7 is an illustration of an exemplary monopolar electrosurgical system in accordance with an embodiment of the present disclosure.

It is to be appreciated that applicator 102 may be any type of cold plasma beam applicator. For example, FIG. 7 shows an exemplary monopolar electrosurgical system generally indicated as 10 comprising an electrosurgical generator (ESU) generally indicated as 12 to generate power for the electrosurgical apparatus 10 and a plasma generator or applicator generally indicated as 14 to generate and apply a plasma stream or beam 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma beam 16. The high frequency electrical energy is fed from the secondary of the transformer 24 through an active conductor 30 to the electrode 28 (collectively active electrode) in the handpiece 26 to create the plasma beam 16 for application to the surgical site 18 on the patient 20. Furthermore, in some embodiments, a current limiting capacitor 25 is provided in series with the electrode 28 to limit the amount of current being delivered to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that, in some embodiments, the transformer 24 may be disposed in the plasma generator handpiece 26. In this configuration, other transformers may be provided in the generator 12 for providing a proper voltage and current to the transformer in the handpiece 26, e.g., a step-down transformer, a step-up transformer or any combination thereof.

It is to be appreciated that in some embodiments, applicator 102 may be a cold plasma applicator with a retractable blade. Such an electrosurgical apparatus is described in commonly owned U.S. Pat. No. 9,060,765, the contents of which are hereby incorporated by reference in its entirety.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A system for fractionated skin resurfacing comprising:

a mask including a top surface and a bottom surface with a plurality of apertures disposed therethrough, each of the plurality of apertures extending from the top surface to the bottom surface, wherein the mask is made of a non-conductive material and the bottom surface is configured to be applied to an area of skin of a patient to be treated; and a cold plasma applicator configured to generate a cold plasma beam for a particular treatment and apply the cold plasma beam to the top surface of the mask, wherein the plurality of apertures of the mask enable the cold plasma beam to contact portions of the area of skin exposed by the plurality of apertures and portions of the mask between each of the apertures produce untreated areas such that the area of skin exposed by the plurality of apertures is affected by the cold plasma beam and areas of skin under the portions of the mask between each of the apertures are untreated, wherein the mask includes a first layer and a second layer, the first layer including the top surface and a thermally insulating material, and the second layer including the bottom surface and made from a material that retains temperatures of the mask below ambient temperature for a period of time, the bottom surface of the second layer contacting the area of skin to be treated, wherein the first layer insulates the second layer from an environment surrounding the mask reducing absorption of heat in the second layer from the surrounding environment to retain the temperature of the second layer for the period of time.

2. The system of claim 1, wherein the mask has a predetermined thickness, a predetermined spacing between each of the plurality of apertures and the plurality of apertures each have a predetermined diameter, and wherein each of the predetermined mask thickness, the predetermined aperture spacing and the predetermined aperture diameter are configured based on the diameter of the generated cold plasma beam.

3. The system of claim 1, wherein the mask is made of a plastic material.

4. The system of claim 1, wherein the first layer of the mask is made of at least one of polyethylene, polypropylene, polystyrene, polyester, polycarbonate, polyvinyl chloride, polysulfone, and/or polyether ether ketone.

5. The system of claim 1, wherein the bottom surface of the second layer includes an adhesive backing configured to enable the mask to adhere to the skin of the patient.

6. The system of claim 1, wherein the mask is configured to be flexible to adapt to the contours of the skin of the patient.

7. The system of claim 1, wherein second layer of the mask is made of a material that retains temperatures of the mask below a predetermined temperature setpoint for extended periods of time such that the skin remains cool during a particular treatment.

8. The system of claim 7, wherein the material is at least one of hydroxyethyl cellulose, sodium polyacrylate, and/or vinyl-coated silica gel.

9. The system of claim 7, wherein the temperature of the mask is lowered prior to applying the mask to the area of skin to be treated to keep the epidermal tissue of the area of skin below the predetermined temperature setpoint during treatment, the predetermined temperature setpoint being the surface temperature of the epidermal tissue of the area of skin to be treated.

10. The system of claim 1, wherein the mask is configured as at least one of a face mask, a sleeve, a glove, and/or a boot.

11. The system of claim 2, wherein the predetermined aperture spacing across a first portion of the mask is less than the predetermined aperture spacing across a second portion of the mask to adjust the amount of plasma per unit area applied to the first portion and the second portion.

12. The system of claim 2, wherein the predetermined diameter of each aperture across a first portion of the mask is smaller than the predetermined diameter of each aperture across a second portion of the mask to adjust the amount of plasma per unit area applied to the first portion and the second portion.

13. The system of claim 1, wherein the first layer of the mask is configured to enable the cold plasma beam to be applied over the top surface of the mask more than once.

14. The system of claim 1, wherein mask is a hand-held card-type mask configured to be held over the area of skin to be treated.

15. The system of claim 14, wherein the hand-held card-type mask includes a handle portion and at least a second portion, the handle portion configured to be gripped by a user and the second portion shaped to facilitate treatment of the skin around at least one body structure of the patient, the plurality of apertures disposed through the second portion.

16. The system of claim 15, wherein the second portion is shaped to facilitate treatment of the skin around at least one of the nose and eye of the patient.

17. The system of claim 16, wherein the hand-held card-type mask further includes a third portion shaped to facilitate treatment of the skin around at least one second body structure of the patient.

18. A system for fractionated skin resurfacing comprising:

a mask including a plurality of apertures disposed through a surface, wherein the mask is made of a non-conductive material and configured to be applied to an area of skin of a patient to be treated;

a cold plasma applicator configured to apply a cold plasma beam to the surface of the mask, wherein the cold plasma beam contacts portions of the area of skin exposed by the plurality of apertures; and a microneedling apparatus to be applied over the surface of the mask to create the plurality of apertures disposed through the surface of the mask and a second plurality of apertures disposed through the area of skin to be treated such that the plurality of apertures disposed through the surface of the mask and the second plurality of apertures disposed through the area of skin to be treated are aligned.

19. The system of claim 18, wherein the mask is configured as a fluid to be applied to the area of skin to be treated, the fluid configured to solidify over the area of skin to be treated after being applied such that the mask is formed.

20. The system of claim 2, wherein the mask is configured as a plurality of strips.

21. The system of claim 2, wherein the predetermined mask thickness is one tenth the diameter of the cold plasma beam, and the aperture spacing and the aperture diameter are less than ten diameters of the cold plasma beam.

22. The system of claim 2, wherein a lower limit of the predetermined mask thickness is based on a material of the mask.

23. The system of claim 2, wherein an upper limit of the predetermined aperture spacing and an upper limit of the predetermined aperture diameter is based on a tradeoff of enhanced recovery time versus achieving a desired physiological effect for the particular treatment.

24. The system of claim 18, wherein the mask includes a bottom surface configured to be applied to an area of skin of a patient to be treated and the bottom surface of the mask includes an adhesive backing configured to enable the mask to adhere to the skin of the patient.

25. The system of claim 18, wherein the microneedling apparatus further comprises a replaceable roller unit including a plurality of microneedle pins configured to create the apertures, wherein the microneedle pins are configured with a predetermined diameter and predetermined spacing between each microneedle pin.

26. The system of claim 25, wherein the microneedling apparatus further includes at least two different replaceable roller units, each roller unit having microneedle pins that are configured with a different predetermined diameter and different predetermined spacing from each other roller unit.

27. The system of claim 18, wherein the fluid is at least one of a spray and cream.

* * * * *